United States Patent
Hoque et al.

(10) Patent No.: US 8,618,499 B1
(45) Date of Patent: Dec. 31, 2013

(54) ELECTRON BEAM IRRADIATION APPARATUS

(71) Applicant: Hitachi High-Technologies Corporation, Tokyo (JP)

(72) Inventors: Shahedul Hoque, Hitachinaka (JP); Hajime Kawano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/788,035

(22) Filed: Mar. 7, 2013

(30) Foreign Application Priority Data

Jul. 18, 2012 (JP) .................................. 2012-159179

(51) Int. Cl.
- *H01J 37/244* (2006.01)
- *H01J 37/256* (2006.01)
- *G01N 23/203* (2006.01)

(52) U.S. Cl.
USPC ..... 250/397; 250/396 R; 250/310; 250/492.2; 250/492.22

(58) Field of Classification Search
USPC .............. 250/397, 396 R, 492.2, 492.22, 310
See application file for complete search history.

(56) References Cited

U.S. PATENT DOCUMENTS

| | | | |
|---|---|---|---|
| 5,708,276 A | 1/1998 | Ohkawa et al. | |
| 6,838,682 B2 * | 1/2005 | Sohda et al. | 250/491.1 |
| 7,171,038 B2 * | 1/2007 | Adler et al. | 382/149 |
| 7,705,304 B2 * | 4/2010 | Kawamata et al. | 250/310 |
| 8,450,215 B2 * | 5/2013 | Mantz et al. | 438/706 |

FOREIGN PATENT DOCUMENTS

JP 09-036019 A 2/1997

OTHER PUBLICATIONS

Reimer, L., "Scanning Electron Microscopy, Physics of Image Formation and Microanalysis", Optical Sciences, Second Edition, pp. 172-181, Springer, 1998.

* cited by examiner

*Primary Examiner* — Nikita Wells
(74) *Attorney, Agent, or Firm* — Miles & Stockbridge P.C.

(57) ABSTRACT

The present invention has for its object to provide an electron beam irradiation apparatus which can suppress influences the electric fields generated by a plurality of backscattered electron detectors have. To attain the above object, an electron beam irradiation apparatus equipped with a scanning deflector comprises a plurality of backscattered electron detectors, a power source for detectors which applies voltages to the plural backscattered electron detectors, respectively, and a controller device which adjusts application voltages the power source for detectors delivers, on the basis of an image shift when the voltages are applied to the plural backscattered electron detectors.

5 Claims, 9 Drawing Sheets

FIG.4A  FIG.4B  FIG.4C
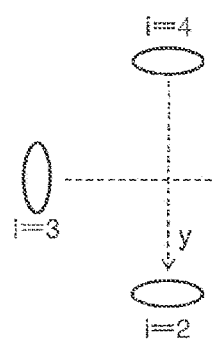 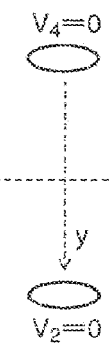 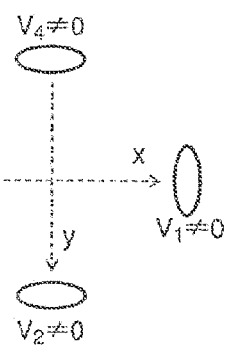
FIG.4D  FIG.4E
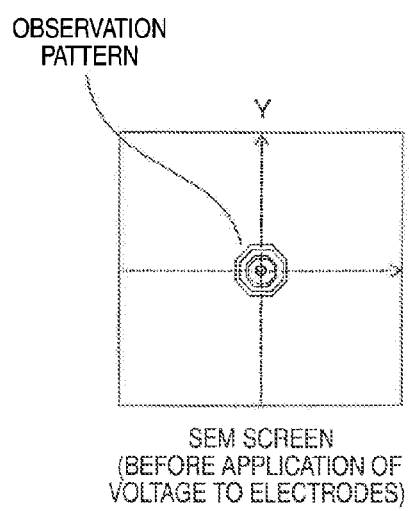 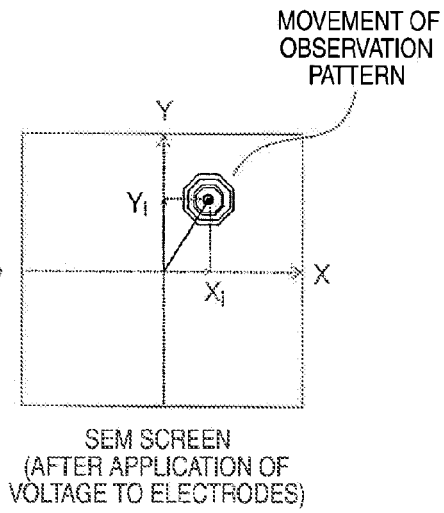

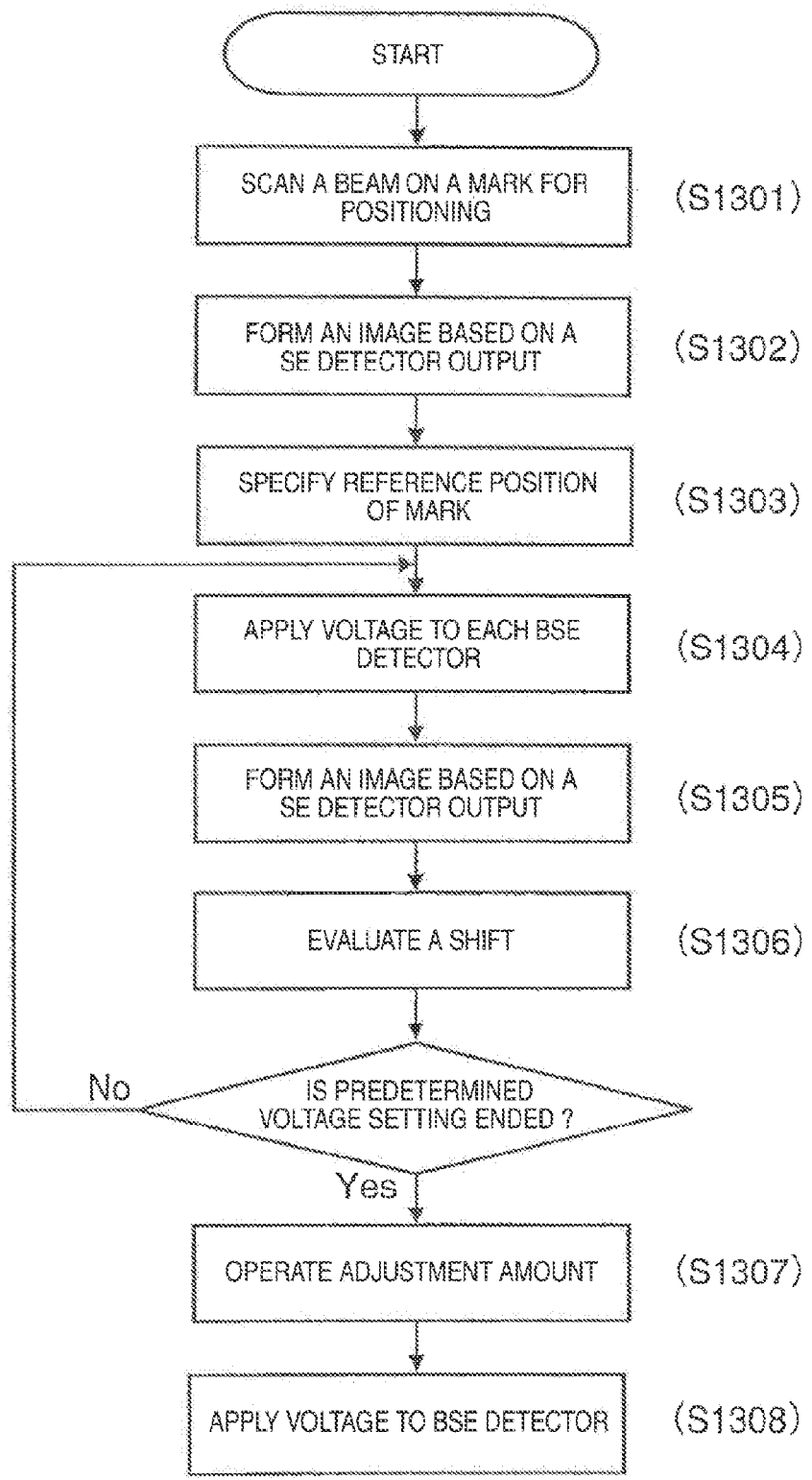

ELECTRON BEAM IRRADIATION APPARATUS

BACKGROUND OF THE INVENTION

The present invention relates to electron beam irradiation apparatuses and more particularly, to an electron beam irradiation apparatus having a plurality of detectors for detection of backscattered electrons.

A scanning electron microscope (SEM) representing one type of electron beam irradiation apparatus detects secondary electrons (SE's) and backscattered electrons (BSE's: hereinafter referred to sometimes as reflected electrons), the SE's and BSE's being given of from a sample under irradiation of an electron beam (hereinafter referred to as a primary electron beam or primary electrons) on the sample. By converting signals of the SE's and BSE's into images and line profiles, the sample can be observed, inspected or measured. Especially, the electron microscope is widely applied to measurement of semiconductor devices and therefore, techniques for the semiconductor device measurement are required to be applicable to patterns of a variety of contours.

JP-A-9-36019 (Corresponding to U.S. Pat. No. 5,708,276) discloses an electron beam irradiation apparatus having 4 reflected electron detectors. The 4 reflected electron detectors are arranged axially symmetrically to the center of an electron beam optical axis to detect reflected electrons given off in the respective directions. Reflected electrons given off in a low angle direction (reflected electrons passing through a trajectory relatively close to the surface of a sample in contrast to reflected electrons passing through a trajectory paraxial to the electron beam optical axis) change their emission directions in accordance with directional situations of edges of a pattern, so that a shade contrast of the pattern can be formed into a distinct image through the use of the plural reflected electron detectors.

On the other hand, in order to detect reflected electrons with high efficiencies, a high voltage of about 10 kV needs to be applied to the detector. With the plural detectors arranged axially symmetrically to the electron beam optical axis as indicated in JP-A-936019, influences the electric fields based on applied voltages have upon the electron beam become axially symmetrical in theory. The inventors, however, studied to find out a possibility that actually, the influences become asymmetrical. This is considered to be caused by errors in assembling the electron microscope and by disturbance external of the electron microscope. The electron microscope will hereafter be required of further higher accuracy and therefore, there is a possibility that an axial misalignment or shift and aberration due to a slight asymmetric status of electric field cannot be neglected.

SUMMARY OF THE INVENTION

An electron beam irradiation apparatus having a plurality of backscattered electron detectors will hereinafter be proposed which aims at suppressing influences of electric fields the detectors generate.

In an embodiment for accomplishing the above object, an electron beam irradiation apparatus equipped with a scanning deflector adapted to scan the electron beam emitted from an electron source will be proposed which comprises a plurality of backscattered electron detectors, power sources for detector adapted to apply voltages to the plural backscattered electron detectors, respectively, and a controller device adapted to adjust the application voltage of the power source for detector on the basis of image shifts caused when the voltages are applied to the plural backscattered electron detectors.

In a more specified embodiment, an electron beam irradiation apparatus will be proposed in which the plural backscattered electron detectors are arranged axially symmetrically to an ideal optical axis of the electron beam.

In a more specified embodiment, an electron beam irradiation apparatus will be proposed in which the controller device adjusts the power sources so that the image shift may be suppressed.

According to the construction as above, in the electron beam irradiation apparatus having the plural backscattered electron detectors, the axial shift due to electric fields generated by the detectors can be suppressed.

Other objects, features and advantages of the invention will become apparent from the following description of the embodiments of the invention taken in conjunction with the accompanying drawings.

BRIEF DESCRIPTION OF THE. DRAWINGS

FIGS. 4A, 4B, 4C, 4D and 4E are diagrams illustrating behavior of shifting of a field of view under application of voltages to the detectors.

FIG. 13 is a flowchart showing a process for determining conditions of voltages-applied to the detectors.

DESCRIPTION OF THE EMBODIMENTS

When observing and measuring a sample by means of a SEM, a probe current needs to be decreased with the aim of reducing a damage of the sample under electron beam irradiation. Since SE's can be caught by a large amount, a small probe current is used ordinarily to cause SE signals to be utilized for generating SEM images. Emission energy of SE's is, however, low and is sensitive to influences the charge and contamination on the sample have upon the SE's and as a result, a topographic (convex and concave) shape of the sample cannot be expressed correctly. Especially, a line of a chip resist will be mistaken for a space and a core of a self-aligned double patterning (SADP) line will be mistaken for a gap, giving rise to problems in measurement of a next-generation device.

Figure 2:
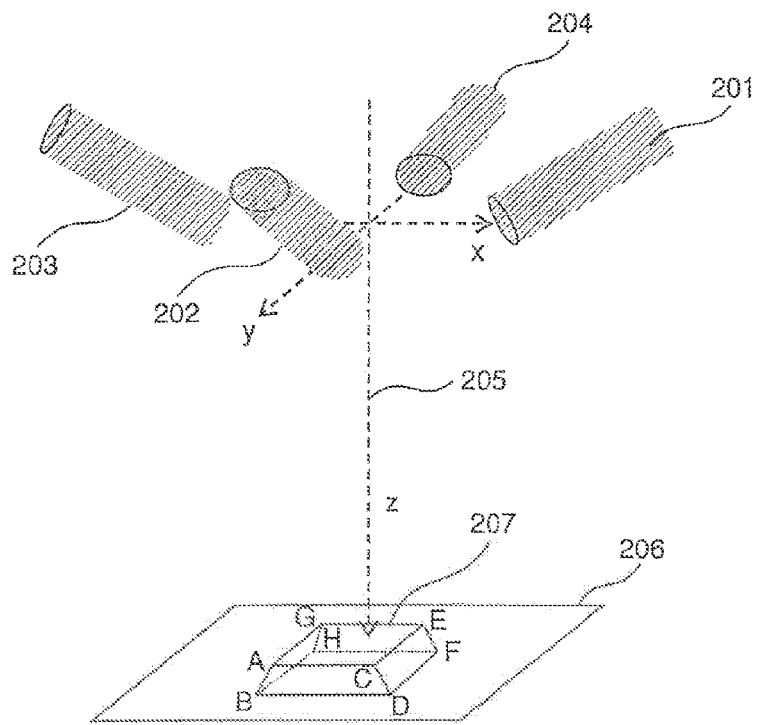
FIG. 2 is a diagram illustrating BSE detectors arranged in 4 directions.

On the other hand, back scattered electrons given off at low angles in relation to the direction of the surface of sample (low angle BSE's) have high energies and pieces of information about the sample surface configuration and therefore, can be effective to solve the problem as above. Especially, when detectors are arranged in many directions to capture BSE's at low angles while keeping their emission angles from the sample unvaried, the topography of the surface can be grasped correctly from the contrasts in shade appearing in the obtained images. Referring first to FIG. 2, an example is illustrated in which 4 BSE detectors are arranged axially symmetrically to an optical axis 205 (an electron beam trajectory when the electron beam is not deflected). With the BSE detectors 201 to 204 arranged at intervals of 90°, topographical information of a pattern 207 on observation sample 206 can be obtained. Many BSE's given of from inclined surfaces CDFE and ABHG of pattern 207 reach the BSE detectors 201 and 203 and as a result, images formed on the basis of outputs of these detectors can eminently express pieces of information indicative of these inclined surfaces. Besides, since the ESE detectors 202 and 204 catch many ESE's given of from inclined surfaces ABDC and GHFE, images from these detectors can eminently express pieces of information indicative of these inclined surfaces.

Various types of low angle BSE detection means are available including an Everhart-Thornley (ET) type detector comprised of fluorescent material, light guide or pipe and photomultiplier tube, a semiconductor detector, an avalanche diode and a multi-channel plate (MCP). Of them, the semiconductor detector has a gain which is too low to discriminate a signal from a dark current (nA order) of the device at a probe current of several pA. The avalanche diode has a high gain but has a so narrow device effective area (for example, about 50%) as to decrease the quantum efficiency, thus encountering a problem that a high SN ratio cannot be obtained. The MPC also has a narrow effective area and a short lifetime (2 to 6 months for use in an in-line SEM) and is therefore unsuitable for the in-line apparatus. Then, the ET type detector having a high gain, a quantum efficiency of 90% or more and a long lifetime is properly utilizable. But, the low angle BSE is defective by having a small signal amount and so, with the aim of improving the SN ratio, adoption of a direct detection scheme is desirable in which such as mesh or reflector is not disposed between a sample (electron beam irradiation spot) and an electron receiving portion (detection surface) of the detector.

On the other hand, since a voltage suitable for the fluorescent material to luminesce is 8 to 10 kV, a voltage of about 10 kV is applied ordinarily to the fluorescent material in the ET type detector. When the detector is close to the primary beam, the primary beam will sometimes be affected by the voltage to suffer from an axial shift. To avoid this inconvenience, it is conceivable to interrupt the voltage of detector from the primary beam by using a mesh electrode at zero voltage but this expedient is unsuited for the direct detection for reasons as below. More particularly, when determining the irradiation energy of primary beam under application of a retarding voltage (a negative voltage applied to the sample), SE and ESE given off from the sample have each an energy of several kV or more. In order to introduce the electrons directly to the detector, a voltage of about 10 kV to be applied to the detector is needed. Accordingly, with the voltage of detector interrupted by means of the mesh, for instance, an electric field for attracting the BSE toward the detector becomes insufficient.

Figure 3:
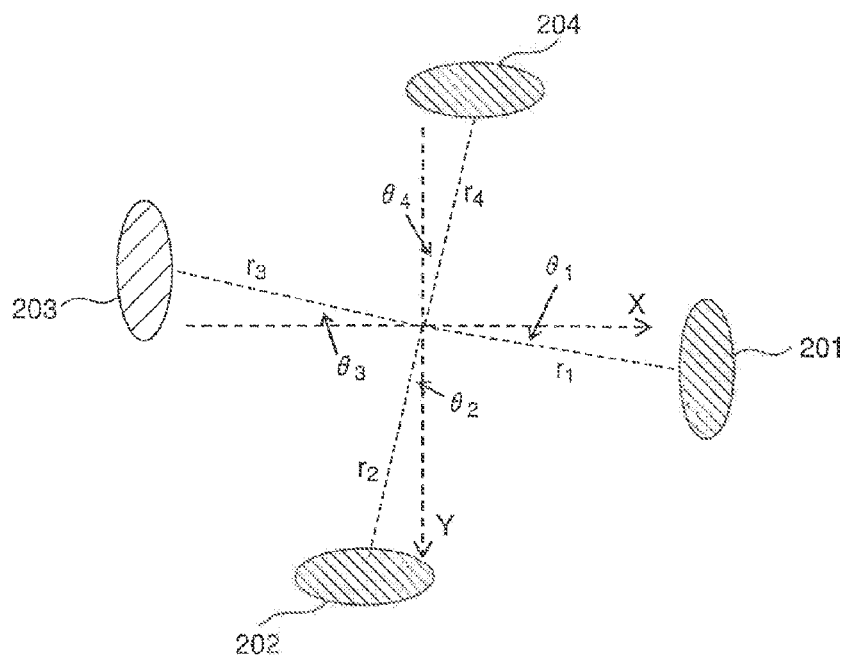
FIG. 3 is a diagram illustrating an example of detectors so arranged as to be shifted from ideal positions.

Thus, when BSE's given off from the sample are attracted by voltages applied to the detectors, the primary beam passing through the same passage as the BSE's also receives deflection action to suffer from axial shifts. With the detectors arranged symmetrically in the 4 directional detection, forces acting on the primary beam passing by the neighborhood of the center will be considered as being balanced so as to prevent axial shift. Practically, however, differences will occur in the distance from the center to the detector and in the arranging angle as well owing to errors in assemblage of the detector and the like factor. This situation is illustrated in FIG. 3. In case that the arrangement of BSE detectors 201 to 204 is set as exemplified in FIG. 3, they will be arranged partly on X axis and on Y axis in design but actually, they are so arranged as to be displaced from the X and Y axes by relative angles of $\theta_1$ to $\theta_4$. In addition, the distances from the optical axis of the electron beam to the individual detectors, which should essentially be identical, are unbalanced or caused to disperse as indicated by $r_1$ to $r_4$. With the same voltage applied to all of the detectors under this condition, forces acting on the primary beam do not balance with one another and a deflection action takes place to generate an axial shift. As a result, the resolution decreases (the primary beam is blurred) owing to a shift of the field of view and a deflection chromatic aberration.

In an embodiment to be described hereinafter, a scanning electron microscope having a plurality of BSE detectors will be described in greater detail as an example of an electron beam irradiation apparatus capable of suppressing the aforementioned factors of reducing the resolution.

In the present embodiment, a scanning electron microscope will be proposed in which in order to prevent the axial shift mainly, voltages applied to the detectors are so adjusted as to nullify the deflection action upon the primary beam. With this construction, the axial shift of primary beam is not avoided by interrupting voltages to the detectors with the help of a mesh electrode at zero voltage but is prevented by making full use of the voltage per se responsible for the cause of the axial shift. As described previously, high voltage applied to the detector is to lighten the fluorescent material but in the apparatus according to the present embodiment, an electric field generated by the application voltage is positively utilized to suppress the axial shift. By directly detecting BSE's according to this method, a high SN ratio can be materialized. Further, by utilizing the application voltage, the aberration correction and focal distance adjustment can also be effected concurrently. In FIG. 3, the number of electrodes N=4 is exemplified but the construction as above can be applicable as far as N≥3 stands.

Figure 1:
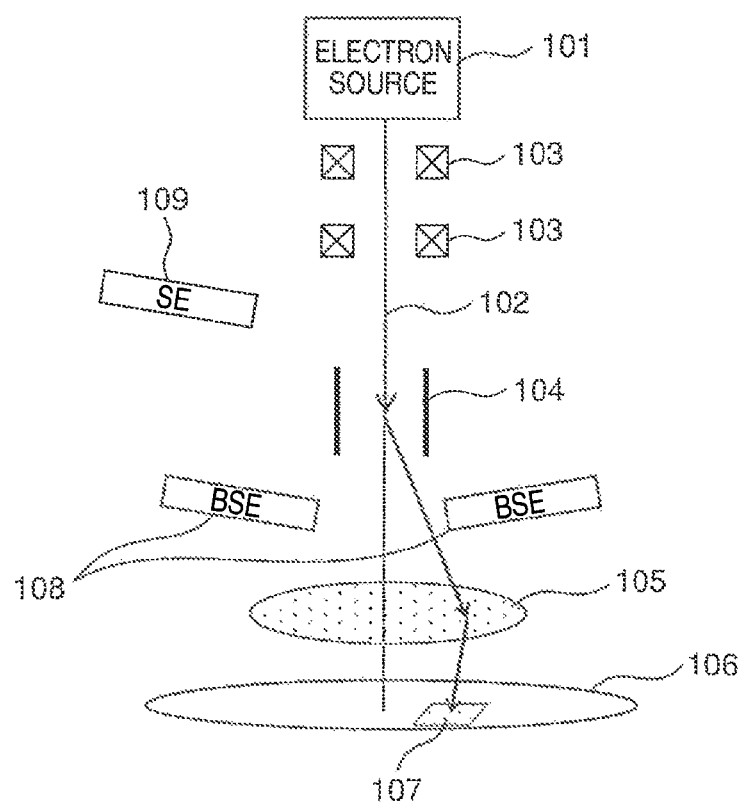
FIG. 1 is a diagram illustrating an example of a scanning electron microscope.

Reverting now to FIG. 1, the scanning electron microscope is illustrated schematically. An electron beam 102 emitted from an electron source 101 is converged by a condenser lens 103 and then, deflected by means of a deflector 104 so as to be scanned on a sample 106. Electrons given off from a scan area 107 of electron beam 102 (a field of view) are captured by BSE detectors 108 and a SE detector 109 so as to undergo image forming or brightness profiling. Three or more BSE detectors 108 are arranged symmetrically to an optical axis of electron beam 102. An objective lens 105 is a lens of final stage arranged immediately before the sample 106 and the beam is focused on the sample by the focusing action the Objective lens 105 has.

Figure 12:
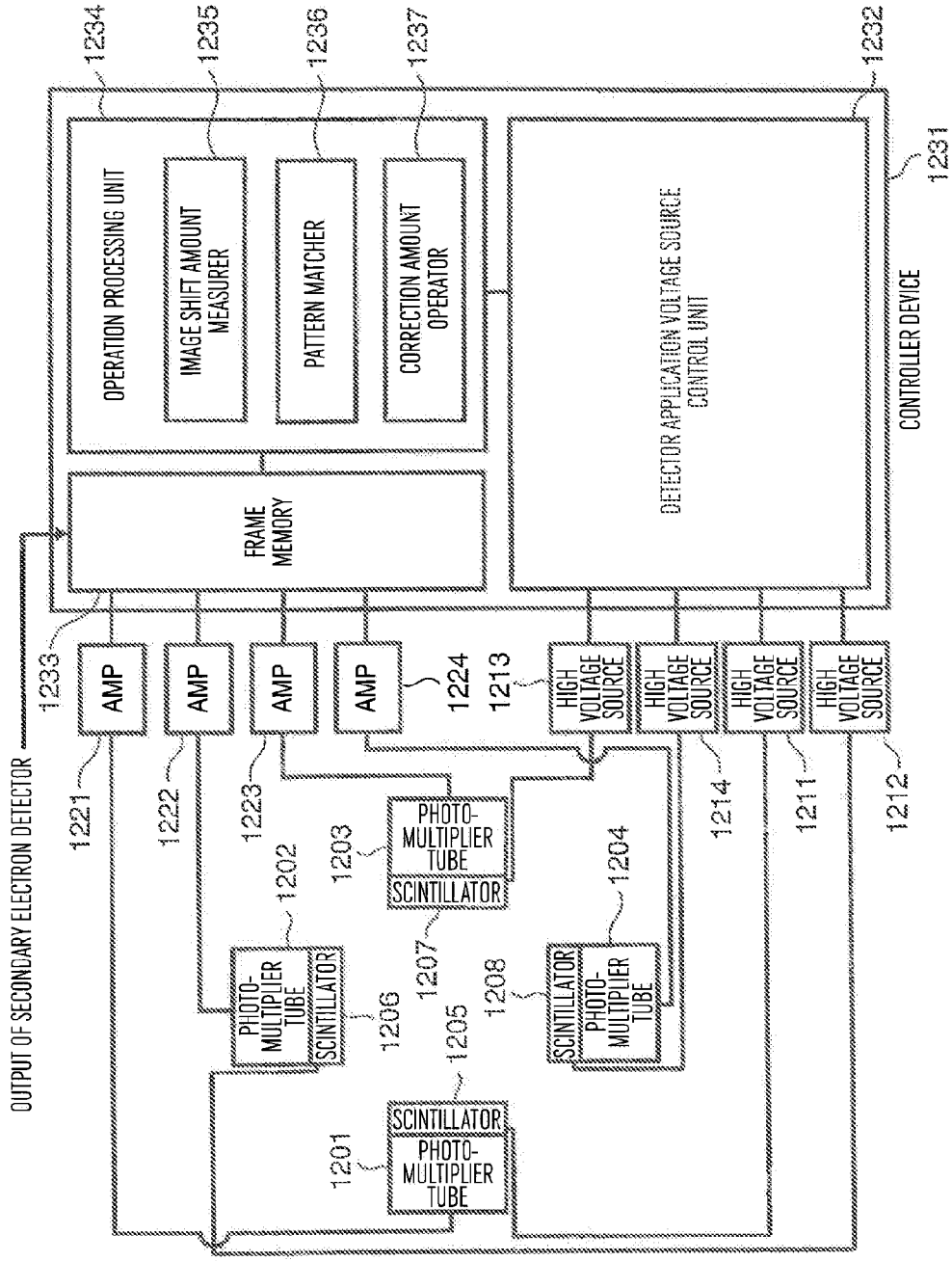
FIG. 12 is a block diagram illustrating an example of the controller device adapted for the scanning electron microscope.

Turning to FIG. 12, details of a controller device 1231 adapted to control the scanning electron microscope are illustrated in block diagram. The scanning electron microscope exemplified in FIG. 12 has 4 BSE detectors. The BSE detectors are constituted by fluorescent materials (scintillators) 1205 to 1208, respectively, and signals converted into light by iii means of the fluorescent materials 1205 to 1208 are subjected to electron amplification by means of photomultiplier tubes 1201 to 1204 each having light guide or pipe so as to be converted into secondary electron signals which in turn are registered in a frame memory 1233 in synchronism with a scanning signal. Outputs of the photomultiplier tubes 1201 to 1204 associated with amplifiers 1221 to 1224, respectively, are amplified thereby and thereafter stored in the frame memory 1233. The frame memory 1233 is so structured as to be able to also store output signals of secondary electron detectors (SE detectors) not shown. The fluorescent materials 1205 to 1208 are connected with variable high voltage sources 1211 to 1214, respectively, and are applied with properly controlled voltages as will be described later. The voltage to be applied to the fluorescent material is a high voltage of about 10 kV and is applied to the fluorescent Material for the purpose of lightening it.

The controller device 1231 receiving the output signals of BSE detectors and delivering control signals for controlling the scanning electron microscope incorporates a detector application voltage source control unit 1232 which generates control signals for controlling the high voltage sources 1211 to 1214 as described previously, the frame memory 1233 and an operation processing unit 1234 which executes operation processes on the basis of signals stored in the frame memory 1233. The operation processing unit 1234 incorporates an image shift amount measurer 1235 adapted to measure a shift ($\Delta x$, $\Delta y$) between patterns displayed in two images (image signals), a pattern matcher 1236 adapted to execute pattern matching by using a template stored in advance in a memory medium not shown, and a correction amount operator 1237 adapted to supply a correction signal (adjustment signal) responsive to the image shift so that voltages corrected on the basis of the image shift amounts may be applied from the high voltage application sources 1211 to 1214 to the individual fluorescent materials.

For detecting ESE's by using the detectors arranged in the plural directions, the detectors will be arranged symmetrically in design but actually; because of, for example, errors in assembling, the arrangement of the plural detectors at positions axially symmetrical to the optical axis will sometimes fails. With voltages $V_0$ applied to all of the detectors concurrently under this condition, the primary beam suffers from an axial shift. Accordingly, a method is proposed according to which the axial shift of primary beam is corrected by adjusting to approximately $V_0$ the voltages to be applied. To add, since a high voltage is applied to the fluorescent material of BSE detector and the fluorescent material applied with the high voltage acts as a deflector for deflecting the beam, the member to be applied with the high voltage will sometimes be expressed as a deflector or an electrode constituting the deflector.

Embodiment 1

In the following description, examples will be described in which by properly adjusting voltages to be applied to the BSE detectors acting as deflectors, an axial shift due to the deflectors will be suppressed. In one example, with the aim for adjusting voltages to be applied to N electrodes (for example, scintillators), voltages to be applied to (N−2) of these electrodes may be fixed and remaining 2 voltages may be adjusted. If all of the N voltages are made variable, a solution cannot be determined definitely and automatic adjustment cannot be executed.

Specifically, an instance of the number of electrodes N=4 will be described (FIG. 4A). Examples applicable to N≥3 can be generalized with ease. When an amount of shift of the primary beam (shift, of field of view or movement of a pattern on the SEM screen) is expressed by ($x_i$, $y_i$), (i=1, 2, 3, 4), under application of voltage to only an i-th electrode (i=1, 2, 3, 4), conditions for preventing the primary beam from axially shifting can be determined by using ($x_i$, $y_i$). Illustrated in FIG. 4B is an instance where voltage is applied to the first electrode only.

In the case of the application voltage being high, direct measurement of ($x_i$, $y_i$) is difficult to achieve. This is because with voltage applied to only one electrode, a blur due to a shift of field of view and to an aberration becomes large and direct measurement of (xi, yi) becomes impossible.

On the other hand, when voltages of substantially the same value are applied to all electrodes at a time, a status balanced to some extent can be set up, with the result that the axial shift of primary electrons can be small and movement of a pattern can be measured on the SEM screen. This condition is illustrated in FIG. 4C. In the figure, application voltages V1, V2, V3 and V4 are of values close to one another. By applying 4 combinational sets of combination of V1 to V4, a shift amount of a combinational set of (Xi, Yi), i=1, 2, 3, 4, corresponding to each combinational set of combination is measured from SEM images and a value of ($x_i$, $y_i$) is extracted by using a value of (Xi, Yi). Examples in the case of a combinational set of (Xi, Yi) are illustrated in FIGS. 4D and 4E. Subsequently, amounts of correction for application voltages are determined by using ($x_i$, $y_i$).

Specifically, adjustment of voltages to be applied to the detectors is carried out in the following order.

(1) Combinational sets of four voltages are applied sequentially to all of the electrodes and shift amounts (Xi, Yi), i=1, 2, 3, 4, are measured (in FIG. 4C, 4 sets of combination of V1 to V4).

(2) From (Xi, Yi), ($x_i$, yi) is calculated.

(3) An adjustment amount $\Delta V$ of voltage is determined.

(4) Validity of the adjustment is confirmed. If the primary beam undergoes an axial shift even after the adjustment, the above procedures are repeated to improve the accuracy of adjustment.

Next, how to determine ($x_i$, $y_i$), (Xi, Yi) and $\Delta V$ will be described. Symbols to be used hereinafter will be summarized as below.

Energy of primary electrons: W,
Voltage to be applied to detector: V,
Speed in lateral direction the primary beam has: v, and
Amount of movement of the primary beam: r.

Even with the voltage applied to the electrode, the final speed of primary electrons in the direction of optical axis z does not change. This is because at the time that the primary electrons enter a region of the electrode, they are accelerated in z direction but upon departure from the region, they are decelerated by a corresponding amount, thus making a z component speed unchanged ultimately. In the following, only a lateral component of speed of the electrons will be taken into account.

Firstly, a method for determining an adjustment amount $\Delta V$ of voltage from ($x_i$, $y_i$) will be explained. When the application voltage to the electrode is changed from V to V+$\Delta V$, the amount of movement of the primary electrons is also changed on the sample. The amount can be estimated as below More particularly, since $W \propto V$ and $W \propto v^2$ can be obtained from electromagnetics and mechanics, respectively and besides, $r \propto \sqrt{V}$ can be obtained from $r \propto v$, with "$V_0$" changed to "$V_0 + \Delta V$", the amount of shift of the primary electrons is changed as indicated by expression (1) by changing $$r \to r\sqrt{1 + \frac{\Delta V}{V_0}} \quad (1)$$

By using this relational expression, the application voltage is so changed as not to cause an axial shift. When voltage $V_0$ is applied to only an i electrode, (i=1, 2, 3, 4), for i=1, V1=$V_0$ standing in FIG. 4B, and the primary beam movement amount is indicated by ($x_i$, $y_i$), the shift amount of the primary electron becomes $$((x_1+x_2+x_3+x_4),(y_1+y_2+y_3+y_4))$$

upon simultaneous application of $V_0$ to all of the electrodes. In general, the above shift amount is not zeroed. Then, a shift amount is considered which is determined when $V_0+\Delta V_1$, $V_0+\Delta V_2$, $V_0+\Delta V_3$ and $V_0+\Delta V_4$ are applied simultaneously to the electrodes 1-4, respectively.

When defining equation (2), $$p_1 = \sqrt{1 + \frac{\Delta V_1}{V_0}} \quad (2)$$

the shift amount of primary electron is determined as below pursuant to expression (1):

$$((p_1x_1+p_2x_2+p_3x_3+p_4x_4),(p_1y_1+p_2y_2+p_3y_3+p_4y_4))$$

In order to prevent the primary beam from shifting axially, $\Delta Vi$ may be adjusted as below.

$$p_1x_1+p_2x_2+p_3x_3+p_4x_4=0$$

$$p_1y_1+p_2y_2+p_3y_3+p_4y_4=0$$

In this adjustment, however, two of $\Delta Vi$ are fixed (may be zeroed) and the remaining two are adjusted. Indicated as below is an instance where
$\Delta V1$ and $\Delta V3$ are fixed (namely, $p_1$ and $p_3$ are known numbers). Then, equations to be solved are $$p_2x_2+p_4x_4=-(p_1x_1+p_3x_3)$$

$$p_2y_2+p_4y_4=-(p_1y_1+p_3y_3)$$

Solutions to the above equations are $$p_2 = \frac{p_1(x_4y_1 + x_1y_4) + p_3(x_4y_3 + x_3y_4)}{x_4y_2 - x_2y_4} \quad (3)\text{-}1$$

$$p_4 = \frac{p_1(x_2y_1 + x_1y_4) + p_3(x_2y_3 + x_3y_2)}{x_4y_2 - x_2y_4} \quad (3)\text{-}2$$

By substituting $p_i$ to equation (2), adjustment amounts $\Delta V_2$ and $\Delta V_4$ are obtained. Equation (2) is reduced to $$\Delta Vi = V_0(p_i^2 - 1) \quad (4)$$

Next, a method for automatically determining an ($x_i$, $y_i$) will be explained. VOltages V1, V2, V3 and V4 are applied concurrently to the electrodes 1, 2, 3 and 4, respectively, as shown in FIG. 4C. The individual voltages V1 to V 4 have, however, values close to one another. In the case of detection in 4 directions, 4 combinational Sets of combination of V1 to V4 are necessary. Pieces of information concerning these combinations are registered in a memory built in, for example, the controller device 1231.

Specifically, the following 4 sets are applied by using ki coefficients which are nearly 1:

First combinational set: $V_0$, $V_0$, $V_0$, $V_0$ (a shift amount of field of view ($X_1$, $Y_1$) at that time is measured from a SEM image)

Second combinational set: $V_0$, $k_1^2V_0$, $V_0$, $V_0$ (a shift amount of field of view ($X_2$, $Y_2$) is measured from a SEM image)

Third combinational set: $V_0$, $V_0$, $k_2^2V_0$, $V_0$ (a shift amount of field of view ($X_3$, $Y_3$) is measured from a SEM image)

Fourth combinational set: $V_0$, $V_0$, $V_0$, $k_3^2V_0$ (a shift amount of field of view ($X_4$, $Y_4$) is measured from a SEM image)

The $k_i$ as above will hereinafter be called a movement amount coefficient.

The following relation is held between $x_i$ and $X_i$.

$$\begin{pmatrix} 1, & 1, & 1, & 1 \\ 1, & k_1, & 1, & 1 \\ 1, & 1, & k_2, & 1 \\ 1, & 1, & 1, & k_3 \end{pmatrix} \begin{pmatrix} x_1 \\ x_2 \\ x_3 \\ x_4 \end{pmatrix} = \begin{pmatrix} X_1 \\ X_2 \\ X_3 \\ X_4 \end{pmatrix}$$

A solution to this determinant is $$\begin{pmatrix} x_1 \\ x_2 \\ x_3 \\ x_4 \end{pmatrix} = \begin{pmatrix} X_1 - X_2 - X_3 - X_4 \\ \frac{-X_1 + 2X_2 + X_3 + X_4}{k_1 - 1} \\ \frac{-X_1 + X_2 + 2X_3 + X_4}{k_2 - 1} \\ \frac{-X_1 + X_2 + X_3 + 2X_4}{k_3 - 1} \end{pmatrix} \quad (5)$$

The $y_i$ can be determined similarly. By substituting ($x_i$, $y_i$) to equation (3), $p_i$ is obtained and a necessary adjustment amount $\Delta V$ is obtained from equation (4).

A process for automatically performing the adjustment of voltages to be applied to the BSE detectors will be described with reference to a flowchart shown in FIG. 13. Firstly, a beam is scanned on a mark for positioning (step 1301) and a secondary electron image (SE image 1) is formed (step 1302). The SE image is stored in the frame memory 1233 and is used for specifying a reference position of the mark (step 1303). Under this condition, voltages are not applied to the individual BSE detectors and therefore, an image is formed which is based on scanning of a beam not affected by electric fields generated by the BSE detectors.

Subsequently, predetermined voltages (for example, $V_0$, $V_0$, $V_0$ and $V_0$) are applied to the individual BSE detectors (step 1304), beam scanning is carried out under this condition to form a SE image 2 and the thus formed image is stored in the frame memory 1233 (step 1305). Next, the image shift amount measurer 1235 measures a shift between the SE image 1 and the SE image 2 (for example, a shift amount (Xi, Yi) of field of view (step 1306). In carrying out measurement of the shift amount of field of view, a SEM image 1, for example, may be registered as a template for pattern matching and is subjected to pattern matching with a SEM image 2 by means of the pattern matcher 1236, thereby determining a shift amount of the pattern, or alternatively, centroid positions of the pattern displayed in the SEM images 1 and 2, respectively, may be specified by using centroid position specifying algorism to determine a distance between the two centroid points ($x_{g2}-x_{g1}$, $y_{g2}-y_{g1}$) as a shift amount of field of view ($X_i$, $Y_i$).

After the shift evaluation as above is executed in respect of individual combinations of voltages applied to the detectors and evaluation based on the voltage setting ends, the correction amount operator 1237 operates voltages (adjusting amounts) to be applied to the individual detectors pursuant to the aforementioned operation expression (step 1307) and on the basis of the adjusting amounts, the detector application voltage control unit 1232 generates control signals for the high voltage sources 1211 to 1214 (step 1308).

Through the above steps, the application voltages to the individual detectors are controlled to ensure that proper application voltages for the individual detectors can be set. It is to be understood that according to the above method of correcting the axial shift by adjusting the application voltages to the detectors, factors responsible for the axial shift per se are corrected and therefore, highly accurate axial shift correction can be made.

Embodiment 2

Figure 5:
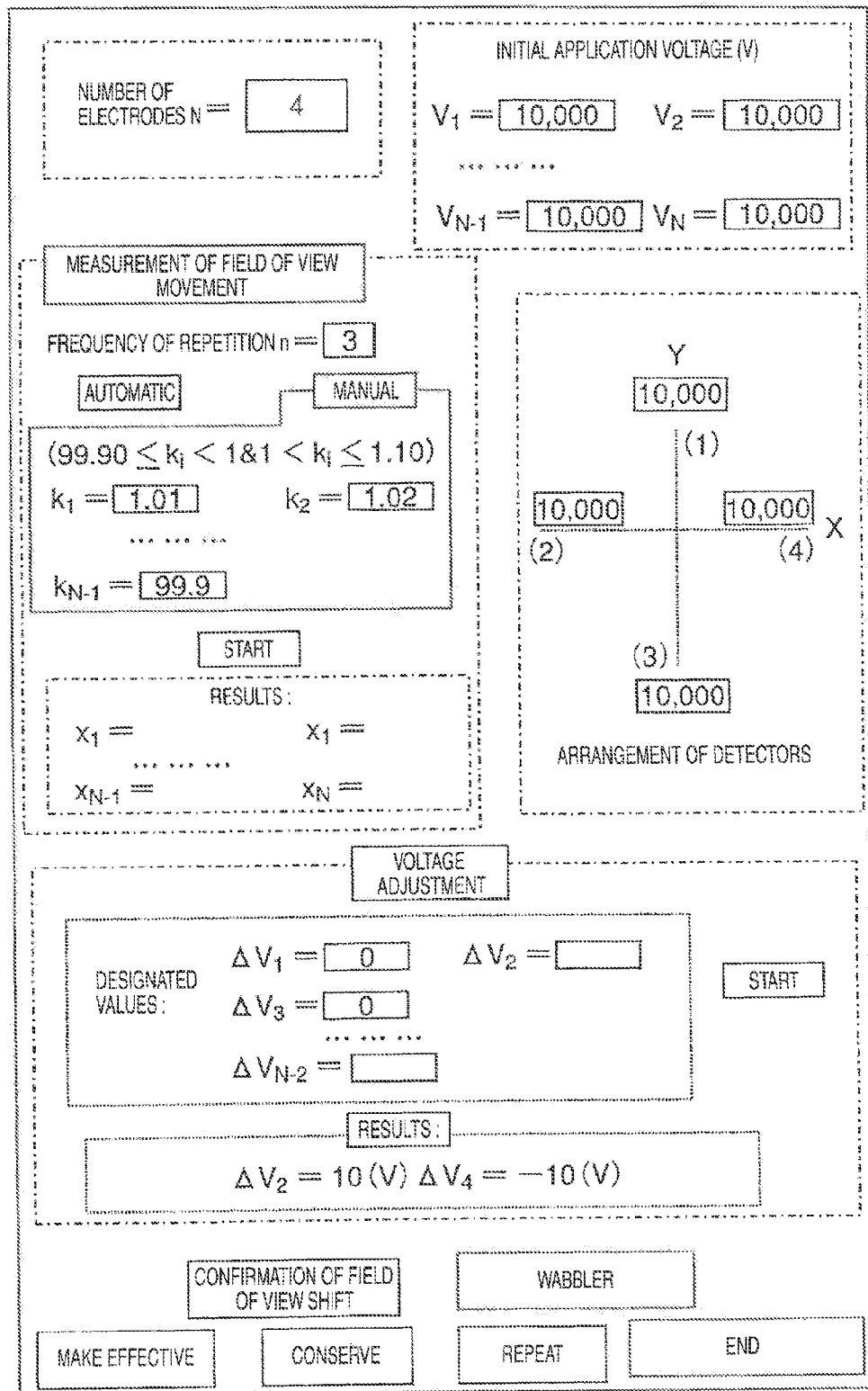
FIG. 5 is a diagram showing an example of a user interface adapted for adjusting voltages applied to the detectors.

Referring now to FIG. 5, an example of a user interface (GUI) will be described which is used when conducting adjustment. The adjustment is carried out in order as below It will be appreciated that a GUI screen exemplified in FIG. 5 is displayed on a display unit not shown. Then, through setting using the GUI screen, operation conditions of the operation condition program stored in the memory built in the controller device 1231 amplified in FIG. 12 are set.

(i) A pattern for marking is moved to the center of screen (FIG. 4D). After voltages are applied to the electrodes, the pattern is moved by an amount corresponding to a shift amount of primary beam ($X_i$, $Y_i$) on an observing sample (FIG. 4E).

(ii) The number of electrodes (N in FIG. 5) is inputted. In this example, an instance of will be described but generally, in the case of N≥3, adjustment can be executed in a similar manner.

(iii) Voltage values to be applied to the individual detectors are inputted. In the example of FIG. 5, all of the voltages are set to 10,000 (V).

(iv) A shift of field of view ($x_i$, $y_i$) is measured. A frequency n of repetition of this measurement is inputted. In the example of FIG. 5, n=3 is set. Subsequently, it is selected by means of button "automatic" or "manual" as to whether measurement of ($x_i$, $y_i$) is carried out automatically or Manually. When "start" is selected after selection of "automatic", automatic measurement of shift amount ($x_i$, $y_i$) is started. In this case, shift amount coefficients ($k_1$, $k_2$, ..., $k_{N-1}$) are set to random values close to 1. Next, automatic length measurement of a shift of field of view ($X_i$, $Y_i$) is carried out and pursuant to expression (5), a shift amount ($x_i$, $y_i$) is calculated. This measurement is repeated n times and an average value of the repetitious measurements is displayed on a column of result and is then, saved or conserved in the memory for the use in later calculation.

When "manual" is selected on the other hand, an area to which coefficients are inputted manually on the GUI is made effective. Since the value of $k_i$ needs to be designated to nearly 1, its range is displayed (in the example of FIG. 5, 0.90≤ki≤1.10). In the event that the input value of $k_i$ exceeds this range, an error message is displayed which urges re-inputting of $k_i$. When a button "start" is selected after all k values are inputted correctly, measurement of ($x_i$, $y_i$) is started. A calculation value of the first measurement is displayed on another window and with n>1 designated, a command to perform a second measurement is given. After the above measurements are conducted n times, an average of the n measurements is displayed on a column of result and for use in the later calculation, stored in the memory, (v) In a column "voltage adjustment" of GUI, an adjusting amount (ΔVi) of voltage to be applied to the electrode is determined.

Firstly, ΔVi settahie freely is inputted. In the example of FIG. 5, ΔV 1=ΔV3=0 is set. With a "start" button depressed subsequently, adjustment coefficients p2 and p3 are calculated pursuant to equation (3) and thereafter, adjustment amounts ΔV2 and ΔV4 are determined by using equation (4) and displayed in a column of "result". In the example of FIG. 5, ΔV2=10 (V) and ΔV4=−10 (V) are set.

(vi) With "make effective" selected, adjusting values determined in (v) are applied to the detectors.

Figure 6:
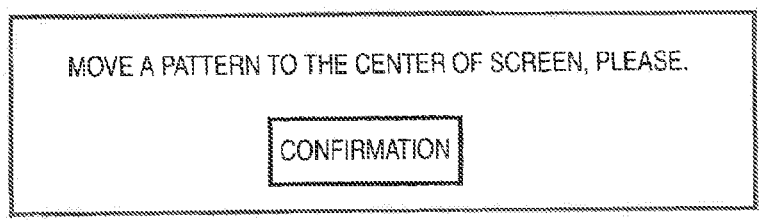
FIG. 6 is a diagram showing an example of a screen adapted for confirming results of voltage adjustment.

(vii) In order to confirm the results of adjustment, two buttons of "confirmation of shift of field of view" and "wabbler" are prepared. With "wabbler" selected, a wabbler used in ordinary axis adjustment (for example, wabbler for objective lens) is operated and accuracy of axial adjustment can be judged from movement of an observation pattern. Further, with "confirmation of shift of field of view" selected, the application voltage to the electrode is once zeroed and a message to the effect "Shift the pattern to the screen center" is displayed (FIG. 6). Under this condition, when a marking pattern is moved to the center of screen (FIG. 4A) and "confirmation" in FIG. 6 is depressed, the voltage inclusive of an adjustment value determined in (v) is applied to the electrode. The accuracy of adjustment can be confirmed from the shift of field of view at that time. When the adjustment succeeds, no shift of field of view will possibly occur after application of the voltage.

(viii) With "save" selected, the adjustment value determined as above is saved to make it effective even when the GUI is closed. With "end" selected, the GUI is closed.

(ix) When the accuracy of adjustment is determined as being insufficient in the above step (vii), "repeat" is selected and the above steps (i) to (vii) are repeated. The initial voltage in the second and succeeding adjustments, however, can be set as necessary to values taking the adjustment value determined immediately before. In this example, with V1=V3=10,000 (V), V2=10,010 (V), and V4=9,990 (V) set, for example, the accuracy of adjustment can further be improved on the basis of the values in the first adjustment. In here, an automatic adjustment might be performed such as repeating above procedure until the shift of filed of view becomes less than a predetermined threshold.

Embodiment 3

Figure 7A:
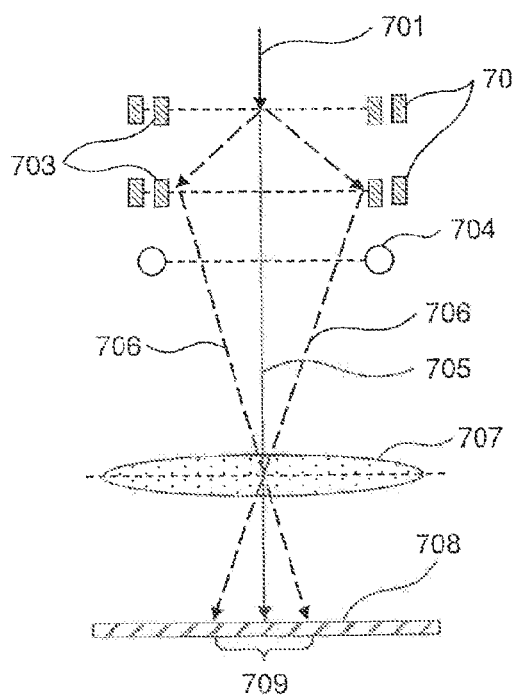
FIGS. 7A and 7B are diagrams illustrating trajectories through which an electron beam travels.
Figure 7B:
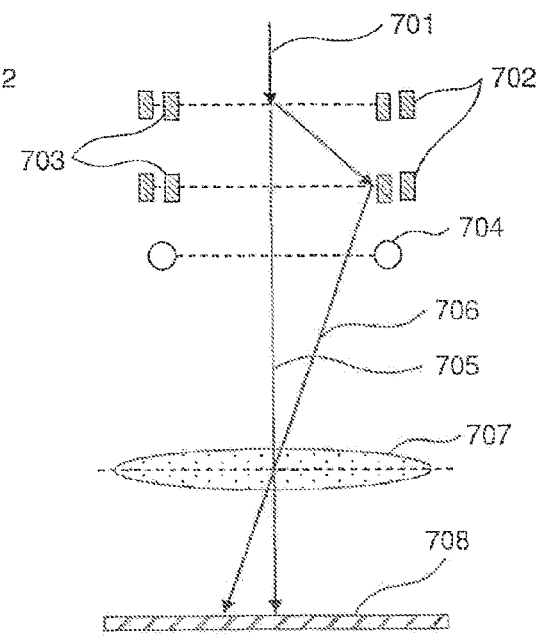

When the field of the scanning of primary beam is wide (low magnification observation) or when the image shift amount (a shift amount of the central primary beam from the optical axis) is large, the amount of adjustment of voltage differs for an area close to the optical axis and for an area distant from the optical axis. In FIG. 7A, a primary beam 701 is deflected by means of a deflector 702, passes through an objective lens 707 and irradiates on a sample 708. A trajectory 705 runs through the optical axis and the primary beam is deflected to the maximum during scanning to travel through a trajectory 706. In FIG. 7B, when the image shift is zero, the trajectory 705 is held but when deflection by the image shifter 703 affects, a trajectory 706 participates. In the case of this example, shifting of the field of view is executed within a field of view movable range 709. The distances from the electrode 704 to the trajectories 705 and 706 differ from each other and strictly, amounts of adjustment of application voltages to the electrode 704 therefore differ. This can be neglected when the difference between the trajectories 705 and 706 is small but when large, cannot be neglected. Accordingly, amounts of misalignment from optical axis the primary beam undergoes are saved in the memory to prepare a reference table. Then, upon execration of observation, an amount of adjustment of the voltage to be applied to the electrode is set from the reference table in accordance with a shift of primary beam from the optical axis.

Figure 8:
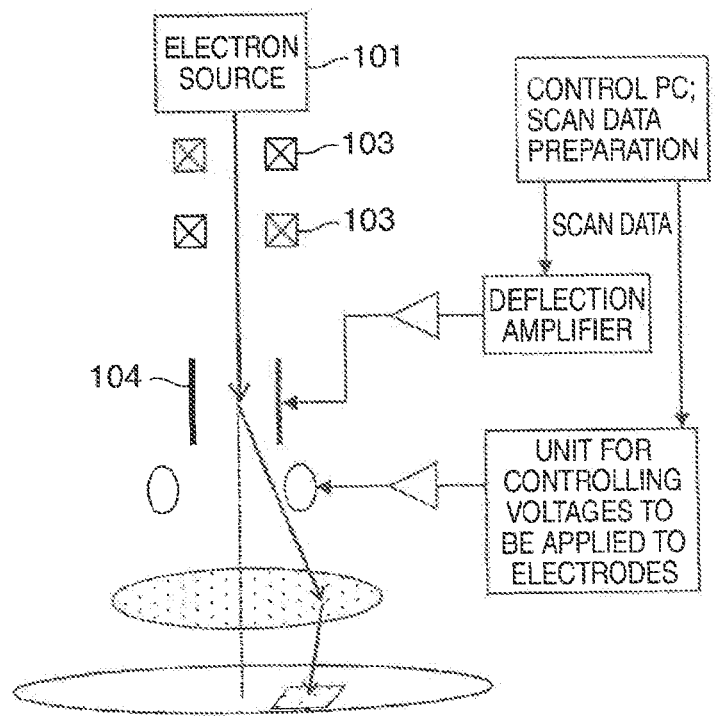
FIG. 8 is a diagram illustrating an example of an electron beam optical system and a system for controlling a scanning signal and a voltage applied to an electrode.

An example of the control system is illustrated in FIG. 8. A control PC prepares scanning data and communicates with the deflector and image shifter to perform scanning of a beam. Concurrently, the scanning data is also communicated to a unit for controlling voltages to be applied to electrodes so that a voltage value commensurate with a scanning amount may be selected from the reference table prepared in advance and may be applied to the electrode.

Embodiment 4

The trajectory of primary electrons is affected by the voltage applied to electrodes and the focal distance changes. When the scan width is wide, an image plane distortion of the objective lens causes a difference in focal distance between the central and peripheral portions of the scan area. Similarly to embodiment 3, axis adjustment and fecal distance adjustment are carried out simultaneously during scanning for the primary beam by applying an adjustment amount commensurate with a distance between the electrode and trajectory.

Embodiment 5

Figure 9:
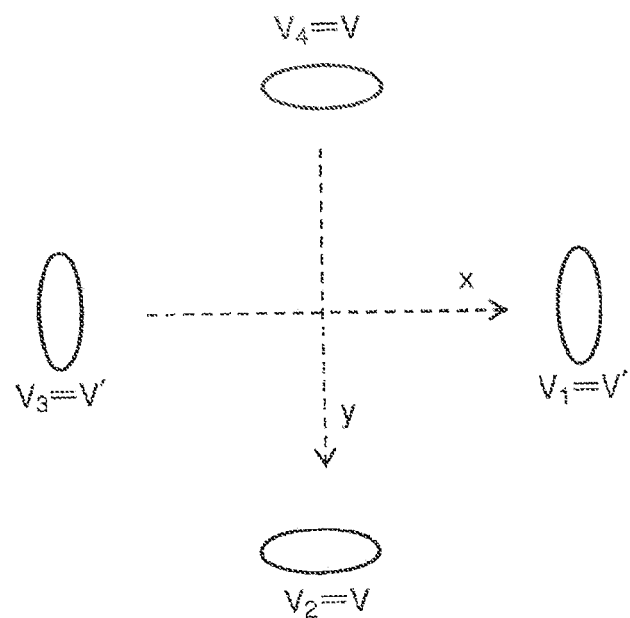
FIG. 9 is a diagram showing an example of setting different values of voltage applied to the electrodes.

While in embodiment 2 all initial voltages are set to the same value (in the example in FIG. 5, 10,000 (V)), the initial voltage can also be set to different values aiming at correcting aberration (for example, distortion). Here, an instance of the number of electrodes being 4 will be described specifically. As shown in FIG. 9, V1=V3=V' and V2=V4=V, for example, are set. Generally, however, V≠V' is held and a ratio therebetween is determined by conditions of aberration correction. In an ideal case, V1 balances with V3, and V2 balances with V4 but practically, owing to errors in assemblage; an axial shift of the primary beam takes place. In order to eliminate the axial shift, the application voltage is adjusted pursuant to the method described in connection with embodiment 1. During the adjustment, however, in (iii) in embodiment 2, initial voltage values V1=V3=V' and V2=V4=V are inputted.

Embodiment 6

Figure 10:
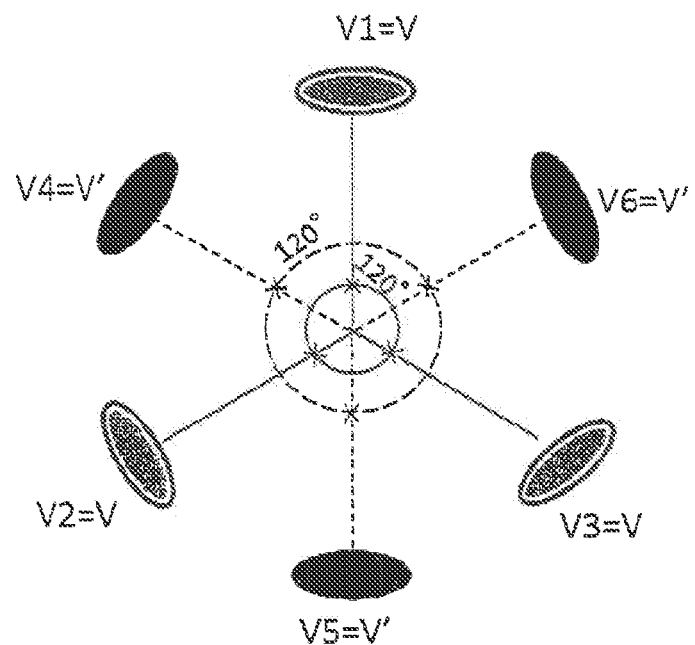
FIG. 10 is a diagram illustrating an example of setting and adjusting application voltages in respect of individual detectors arranged axially symmetrically.

The method described in connection with embodiments 1 and 2 can be extended to the number of electrodes NM (N≥3, M≥1) in general. In this case, N electrodes constitute one set and an angle between adjacent electrodes amounts to $2\pi\text{rad}/N$. The detector having M sets as above are arranged to perform detections in NM directions. Illustrated in FIG. 10 is an example of N=3 and M=2. Application voltages are V1=V2=V3=V and V4=V5=V6=V' (V=V' or V≠V') and voltages can be adjusted in respect of the individual N sets (in the example of FIG. 10, V1, V2 and V3 constitute one set and V4, V5 and V6 constitute another set). Generally, adjustment is effected in connection with respective N sets of electrode/detector, making the degree of freedom. $\Delta Vi$ equal to (N−2) M. This degree of freedom can be applied to, for example, aberration correction.

Embodiment 7

The application of voltages to electrodes is effected in respect of individual energies of the primary beam and individual optical modes of the microscope and values of applied voltages are saved or conserved. When the irradiation energy and optical mode is changed, a value conserved is brought into effectiveness.

Embodiment 8

In the case of the number of electrodes to be adjusted being N, an N−2 number of $\Delta Vi$ values can be set freely. This value of N−2 is set to a value necessary for aberration correction so that the axis adjustment and the aberration correction may be carried out concurrently.

Embodiment 9

By changing M in the detection in NM directions as described in embodiment 6, the number of division of direction in the detection system can be changed. For example, in the detection system of FIG. 10, M=2 stands to provide 6 divisions but when M=1 is set (namely, one set of detectors in N=3 is turned off), the number of division changes to 3. Adjustment of voltage in the detection system is carried out in advance in respect of the individual sets of N=3 as described in embodiment 6, As a result, the primary beam can be prevented from shifting axially under the application of voltages of each set. With the adjustment effected in this manner, readjustment of application voltage can be unneeded when the number of division of direction in the detection system is changed by changing M (through turn-off of detector).

Embodiment 10

Figure 11:
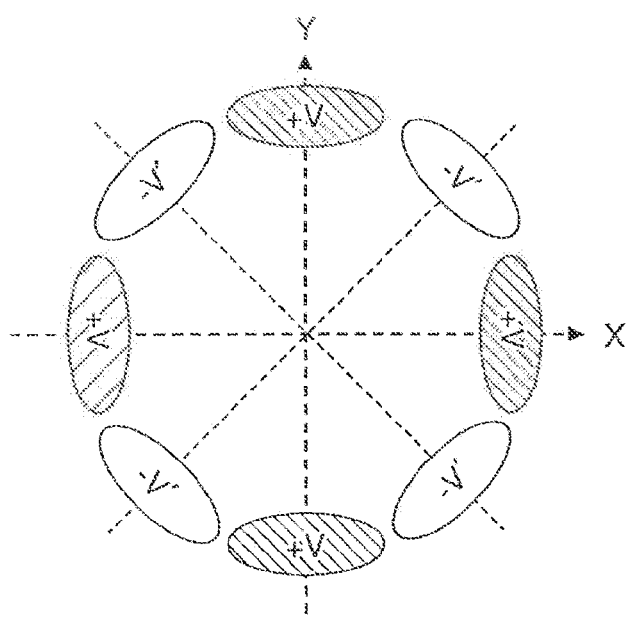
FIG. 11 is a diagram illustrating supplemental electrodes arranged in addition to the detectors.

In the detection system, a supplemental electrode can be interposed between adjacent detectors. An example of detection in 4 directions is illustrated in FIG. 11. With negative voltage applied to the supplemental electrodes, the secondary electrons given off from the sample are not attracted to the supplemental electrodes and can reach the detectors Without losing information indicative of directivity. In FIG. 11, voltage V is applied to the detectors and voltage V' is applied to the supplemental electrodes. The structure as above can be applied to correction of aberration of the primary beam. The voltage to be applied to the supplemental electrode is determined conditions of aberration correction, in order to prevent the primary beam from shifting axially, the voltage to be applied is adjusted according to the method described in embodiments 2 and 6. Different voltages may otherwise be applied to all of the detectors.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An electron beam irradiation apparatus equipped with a scan deflector adapted to scan an electron beam emitted from an electron source, comprising:
    a plurality of backscattered electron detectors;
    a power source for detectors which applies voltages to the plural backscattered electron detectors, respectively; and
    a controller device which adjusts application voltages that said power source applies to said plural backscattered electron detectors on the basis of an image shift.

2. An electron beam irradiation apparatus according to claim 1, wherein said plural backscattered electron detectors are arranged axially symmetrically to an ideal optical axis of the electron beam.

3. An electron beam irradiation apparatus according to claim 1, wherein said controller device so adjusts said power source as to suppress the image shift.

4. An electron beam irradiation apparatus according to claim 1, wherein said backscattered electron detector includes a scintillator applied with voltage.

5. An electron beam irradiation apparatus according to claim 1, wherein said controller device includes a memory for storing a plurality of combinational sets of voltages to be applied to said plural backscattered electron detectors and adjusts, on the basis of a plurality of image shifts obtained when the different sets of voltages are applied, the application voltages said power source for detectors delivers.

* * * * *